(12) United States Patent
Sprenger

(10) Patent No.: US 9,217,133 B2
(45) Date of Patent: Dec. 22, 2015

(54) PREVENTION OF OPPORTUNISTIC INFECTIONS IN IMMUNE-COMPROMISED SUBJECTS

(75) Inventor: Norbert Sprenger, Savigny (CH)

(73) Assignee: Nestec S.A., Vevey (CH)

( * ) Notice: Subject to any disclaimer, the term of this patent is extended or adjusted under 35 U.S.C. 154(b) by 540 days.

(21) Appl. No.: 12/808,053

(22) PCT Filed: Dec. 5, 2008

(86) PCT No.: PCT/EP2008/066850
§ 371 (c)(1),
(2), (4) Date: Jun. 14, 2010

(87) PCT Pub. No.: WO2009/077352
PCT Pub. Date: Jun. 25, 2009

(65) Prior Publication Data
US 2010/0260720 A1 Oct. 14, 2010

(30) Foreign Application Priority Data

Dec. 17, 2007 (EP) .................................... 07123390

(51) Int. Cl.
*C12N 1/20* (2006.01)
*A61K 31/702* (2006.01)
*A61K 35/74* (2015.01)
*A61K 35/745* (2015.01)

(52) U.S. Cl.
CPC ................ *C12N 1/20* (2013.01); *A61K 31/702* (2013.01); *A61K 35/74* (2013.01); *A61K 35/745* (2013.01)

(58) Field of Classification Search
None
See application file for complete search history.

(56) References Cited

U.S. PATENT DOCUMENTS

| | | | | |
|---|---|---|---|---|
| 5,902,743 A * | 5/1999 | Luchansky et al. | ......... | 435/252.1 |
| 6,045,854 A * | 4/2000 | Prieto et al. | .................... | 426/658 |
| 8,197,872 B2 * | 6/2012 | Mills et al. | .......................... | 426/3 |
| 8,394,370 B2 * | 3/2013 | Garcia-Rodenas et al. | .......................... | 424/93.45 |
| 2009/0305996 A1 * | 12/2009 | Beermann et al. | ............... | 514/23 |

FOREIGN PATENT DOCUMENTS

| | | | | |
|---|---|---|---|---|
| EP | 0199535 | 10/1986 | | |
| EP | 0577903 | 1/1994 | | |
| EP | 2072053 | * 12/2007 | ............. | A61K 35/74 |
| EP | 0768375 | 10/2010 | | |
| WO | WO9700078 | 1/1997 | | |
| WO | WO9956754 | 11/1999 | | |
| WO | WO0053200 | 9/2000 | | |

OTHER PUBLICATIONS

LoCascio et al., Journal of Agricultural and Food Chemistry, vol. 55, pp. 8914-8919, 2007, Supporting Information, p. 1-3.*
LoCascio et al., J. Agricultural and Food Chemistry, vol. 55, pp. 8914-8919, 2007, Supporting Information, pp. 1-3.*
Cravioto et al., Journal of Infectious Diseases, vol. 163, No. 6, 1991, pp. 1247-1255.*
ATCC product information: ATCC 27536, retrived from the Internet: www.straininfo.net/strains/37980/browser.*
ATCC product information: ATCC BAA-999, retrieved from the Internet: www.atcc.org/products/all/BAA-999.aspx.*
Thalia et al., retrieved from the Internet Apr. 2, 2015: http://www.mothering.com/forum/363-breastfeeding-challenges/758012-do-i-really-have-foremilk-hindmilk-imbalance-update-apparently-yes-see-post-14-a.html.*
Jarrow et al., retrieved from the Internet Apr. 2, 2015: http://www.nutrivene.com/view_item.php?id=123.*
Gronlund et al., Clinical and Experimental Allergy, vol. 37, pp. 1764-1772, 2007.*
Chaturvedi et al., Glycobiology, vol. 11, No. 5, pp. 365-372, 2001.*
International Search Report for International Application No. PCT/EP2008/066850 mailed on Dec. 2, 2009.
Written Opinion for International Application No. PCT/EP2008/066850 mailed on Dec. 2, 2009.
Morrow, et al., "Human milk oligosaccharide blood group epitopes and innate immune protection against campylobacter and calicivirus diarrhea in breastfed infants," Advances in Experimental Medicine and Biology, vol. 554, 2004, pp. 443-446, XP009096074.
Newburg, et al., "Innate protection conferred by fucosylated oligosaccharides of human milk against diarrhea in breastfed infants," Glycobiology, vol. 14, No. 3, 2004, pp. 253-263, XP002471649.
Morrow, et al., "Human-Milk Glykans That Inhibit Pathogen Binding Protect Breast-feeding Infants against Infectious Diarrhea," The Journal of Nutrition, vol. 135, No. 5, May 2005, pp. 1304-1307, XP002471650.
Lo Cascio, et al., "Glykoprofiling of Bifidobacterial Consumption of Human Milk Oligosaccharides Demonstrates Strain Specific, Preferential Consumption of Small Chain Glykans Secreted in Early Human Lactation," J. Agric. Food Chem., vol. 55, No. 22, Oct. 31, 2007, pp. 8914-8919, XP002471651.
Salminen, et al., "Probiotics: how should they be defined?" Trends in Food Science & Technology, vol. 10, 1999, pp. 107-110.
Matsumoto, et al., "Oral administration of Bifidobacterium longum prevents gut-derived Pseudomonas aeruginosa sepsis in mice," Journal of Applied Microbiology, vol. 104, No. 3, Oct. 2007, pp. 672-680.

* cited by examiner

Primary Examiner — Allison Fox
Assistant Examiner — Yvonne Pyla
(74) Attorney, Agent, or Firm — K&L Gates LLP

(57) ABSTRACT

This invention relates to a composition suitable for use in the prevention of opportunistic infections in immune-compromised individuals comprising a probiotic *Bifidobacterium lactis*, *Bifidobacterium infantis*, *Bifidobacterium breve* or *Bifidobacterium longum* and a fucosylated oligosaccharide selected from the group comprising 2'-fucosyllactose, 3'fucosyllactose, difucosyllactose, lacto-N-fucopentaose, lacto-N-fucohexaose, fucosyllacto-N-hexaose and fucosyllacto-N-neohexaose. The invention further extends to the use of such a composition in the prevention of opportunistic infections in immune-compromised individuals.

7 Claims, No Drawings

PREVENTION OF OPPORTUNISTIC INFECTIONS IN IMMUNE-COMPROMISED SUBJECTS

FIELD OF THE INVENTION

This invention relates to the prevention of opportunistic infections in immune-compromised subjects, particularly premature and neo-natal infants.

BACKGROUND OF THE INVENTION

The immune system of a healthy new-born infant is not as effective as that of an older healthy child or a healthy adult. To a great extent, this is because the newborn infant has yet to encounter potential antigens and the B cells and T cells have yet to mature such that they can mount appropriate immune responses. The newborn infant is not completely unprotected against pathogens because maternal antibodies of the IgG class cross the placenta during pregnancy and remain in the infant for several months. Further, the colostrum produced in the first few days after birth and the milk which succeeds it are rich in maternal antibodies of the IgA class. This natural passive immunity in effect "buys time" for infants who encounter common pathogens in the first few weeks after birth as the maternal antibodies confer a degree of immunity on the baby whilst the baby's own immune system is activated.

However, the immune system of some otherwise healthy neonates may not be fully mature at birth with the result that the infant will be even slower starting to mount its own immune responses even than an infant born with a fully mature immune system. This problem is seen at its most severe in preterm infants. Such infants may be considered to be immune-compromised to some degree. Immune-compromised subjects are in general at risk of infection by opportunistic pathogens such as *Pseudomonas aeruginosa* which may cause infections of the urinary and respiratory tracts for example.

Further, although mother's milk is recommended for all infants in some cases breast feeding is inadequate or unsuccessful for medical reasons or the mother chooses not to breast feed. Infant formulas have been developed for these situations.

In the recent past, certain strains of bacteria have attracted considerable attention because they have been found to exhibit valuable properties for man if ingested. In particular, specific strains of the genera Lactobacilli and Bifidobacteria have been found to be able to colonise the intestinal mucosa, to reduce the capability of pathogenic bacteria to adhere to the intestinal epithelium, to have immunomodulatory effects and to assist in the maintenance of well-being. Such bacteria are sometimes called probiotics. They may be incorporated in nutritional products such as infant formulae.

Extensive studies have peen carried out to identify new probiotic strains. For example, EP 0 199 535, EP 0 768 375, WO 97/00078, EP 0 577 903 and WO 00/53200 disclose specific strains of Lactobacilli and Bifidobacteria and their beneficial effects.

Recently, Matsumoto et al have reported that certain probiotic bacteria, particularly Bifidobacteria were effective in protecting mice against gut-derived sepsis caused by *Pseudomonas aeruginosa* (J. Appl. Microbiol, 2007). The authors comment that this discovery may offer the possibility of developing an alternative therapy to antibiotics, particularly given that bacteria such as *P. aeruginosa* are becoming increasingly resistant to antibiotics.

From the foregoing, it may be seen that there is a need for an effective method for the prevention of opportunistic infections in immune-compromised subjects, particularly premature and neo-natal infants which does not rely on the use of antibiotics and which may be conveniently and safely administered.

SUMMARY OF THE INVENTION

The present inventors have surprisingly found that the co-administration of certain probiotic Bifidobacteria and a fucosylated oligosaccharide is particularly effective in the prevention of opportunistic infections in immune-compromised individuals such as preterm and neonatal infants.

Accordingly, in a first aspect, the present invention provides a composition suitable for use in the prevention of opportunistic infections in immune-compromised individuals comprising a probiotic *Bifidobacterium lactis, Bifidobacterium infantis, Bifidobacterium breve* or *Bifidobacterium longum* and a fucosylated oligosaccharide selected from the group comprising 2'-fucosyllactose, 3'fucosyllactose, difucosyllactose, lacto-N-fucopentaose, lacto-N-fucohexaose, fucosyllacto-N-hexaose and fucosyllacto-N-neohexaose.

In a second aspect, the present invention provides the use of a probiotic *Bifidobacterium lactis, Bifidobacterium infantis, Bifidobacterium breve* or *Bifidobacterium longum* and a fucosylated oligosaccharide selected from the group comprising 2'-fucosyllactose, 3'fucosyllactose, difucosyllactose, lacto-N-fucopentaose, lacto-N-fucohexaose, fucosyllacto-N-hexaose and fucosyllacto-N-neohexaose in the manufacture of a composition for the prevention of opportunistic infections in immune-compromised individuals.

The invention further extends to a method for the prevention of opportunistic infections in immune-compromised individuals which comprises administering to an individual in need thereof a therapeutic amount of a probiotic *Bifidobacterium lactis, Bifidobacterium infantis, Bifidobacterium breve* or *Bifidobacterium longum* and a fucosylated oligosaccharide selected from the group comprising 2'-fucosyllactose, 3'fucosyllactose, difucosyllactose, lacto-N-fucopentaose, lacto-N-fucohexaose, fucosyillacto-N-hexaose and fucosyllacto-N-neohexaose.

Without wishing to be bound by theory, the inventors believe that the efficacy of the combination of probiotic and fucosylated oligosaccharide described above in the prevention of opportunistic infections in immune-compromised subjects may be a result of synergies between the specific probiotic and oligosaccharide. It is known that human milk contains a complex array of oligosaccharides including fucosylated and sialylated species. The functions of all these oligosaccharides have not yet been fully elucidated but it has been hypothesised that one of their functions is to act as a metabolic fuel for the intestinal microbiota. An optimal intestinal microbiota for human infants is dominated by various species of Bifidobacteria and it had been thought that one of the functions of the oligosaccharides in human milk was to serve as a fermentation substrate and/or metabolic stimulus specifically for Bifidobacteria, thereby favouring growth and/or metabolic activity of these species at the expense of less desirable anaerobes such as Clostridia and Bacteroides. However, it now seems that only certain Bifidobacteria, specifically *Bifidobacterium lactis, Bifidobacterium infantis, Bifidobacterium breve* or *Bifidobacterium longum* are stimulated by fucosylated oligosaccharides such as 2'fucosyllactose which is an abundant component of human milk. At the same time, adhesins from *Pseudomonas aeruginosa* for example recognise fucose epitopes such that fucose epitopes in the intestinal lumen may act as a "decoy" for these adhesins preventing them from binding to their natural ligands and thereby reducing the risk of infection. By supplying a combination of a probiotic *Bifidobacterium lactis, Bifidobacterium infantis, Bifidobacterium breve* or *Bifidobacterium longum* and a fucosylated oligosaccharide which can stimulate the probiotic, the inherent ability of the probiotic to suppress the adhesion of the pathogen is boosted whilst at the same time the fucose epitopes and Bifidobacteria metabolites provide a separate line of defense against pathogen adhesion.

DETAILED DESCRIPTION OF THE INVENTION

In this specification, the following terms have the following meanings:

"follow-on formula" means a foodstuff intended for particular nutritional use by infants aged over four months and constituting the principal liquid element in the progressively diversified diet of this category of person;

"growing up milk" means a milk based beverage adapted for the specific nutritional needs of young children;

"immune-compromised individual" means an individual with an immune system which is immature or otherwise not fully effective such that the individual is vulnerable to infection by opportunistic pathogens;

"infant" means a child under the age of 12 months;

"infant formula" means a foodstuff intended for particular nutritional use by infants during the first four to six months of life and satisfying by itself the nutritional requirements of this category of person;

"neonatal infant" means a full-term infant under the age of one month;

"opportunistic pathogen" means a pathogen which has no effect on a healthy individual but which can cause a variety of infections in an immune-compromised individual;

"prevention of opportunistic infections" includes reduction of risk and/or severity of such infections;

"probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999; 10 107-10).

All percentages are by weight unless otherwise stated.

The immune-compromised individual may be a premature or neonatal infant. Alternatively, the immune-compromised individual may be an older child or adult with an immune system which is not fully effective as a result of an existing condition or illness such as infection with human immunodeficiency virus (HIV) or as a result of therapy for an existing condition such as immuno-suppressive drugs for the treatment of auto-immune conditions eg Crohn's disease or rheumatoid arthritis or chemo-therapy for the treatment of cancer.

Suitable probiotic Bifidobacteria include *Bifidobacterium lactis* CNCM I-3446 sold inter alia by the Christian Hansen company of Denmark under the trade mark Bb12, *Bifidobacterium longum* ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V, the strain of *Bifidobacterium breve* sold by Institut Rosell (Lallemand) under the trade mark R0070 and the strain of *Bifidobacterium infantis* sold by Procter & Gamble Co. under the trade mark Bifantis.

A suitable daily dose of the probiotic bacteria is from 10e3 to 10e12 colony forming units (cfu), more preferably from 10e7 to 10e11 cfu.

As noted above, the fucosylated oligosaccharide may be selected from the group comprising 2'-fucosyllactose, 3'fucosyllactose, difucosyllactose, lacto-N-fucopentaose, lacto-N-fucohexaose, fucosyllacto-N-hexaose and fucosyllacto-N-neohexaose. A particularly preferred fucosylated oligosaccharide is 2'-fucosyllactose (2FL).

The fucosylated oligosaccharide may be isolated by chromatographic or filtration technology from a natural source such as animal milks. Alternatively, it may be produced by biotechnology using specific fucosyltransferases and/or fucosidases either by enzyme based fermentation technology (recombinant or natural enzymes) or by microbial fermentation technology. In the latter case microbes may either express their natural enzymes and substrates or may be engineered to produce respective substrate; and enzymes. Single microbial cultures and/or mixed cultures may be used. Fucosylated oligosaccharide formation can be initiated by acceptor substrates starting from any degree of polymerisation (DP) from DP=1 onwards. Alternatively, fucosylated oligosaccharides may be produced by chemical synthesis starting with lactose and free fucose. Fucosylated oligosaccharides are also available for example from Kyowa Hakko Kogyo of Japan.

The fucosylated oligosaccharide and probiotic Bifidobacteria may be administered in the same composition or may be administered sequentially.

The opportunistic infections which may be prevented according to the invention include infections of the respiratory, urinary or gastrointestinal tracts by *Acinetobacter baumannii, Staphylococcus aureus, Clostridium difficile, Pseudomonas aeruginosa* or *Candida albicans* for example. The invention is particularly suitable for the prevention of opportunistic infections including necrotising enterocolitis in premature or neonatal infants. The invention is also suitable for the prevention of nosocomial infections in immune-compromised subjects.

If infants are to be addressed, the composition is preferably an infant formula.

Preferably an infant formula according to the invention contains from 0.1 to 3 g fucosylated oligosaccharide/100 g infant formula on a dry weight basis and from 10e3 to 10e12 cfu/g infant formula, more preferably 10e6 to 10e9 cfu/g of the probiotic *Bifidobacterium lactis, Bifidobacterium infantis, Bifidobacterium breve* or *Bifidobacterium longum.*

An infant formula according to the invention preferably further contains at least one prebiotic in an amount of 0.3 to 10%. A prebiotic is a non-digestible food ingredient that beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS). A combination of prebiotics may be used such as 90% GOS with 10% short chain fructo-oligosaccharides such as the product sold under the trade mark Raftilose® or 10% inulin such as the product sold under the trade mark Raftiline®. A particularly preferred combination of prebiotics is 70% short chain fructo-oligosaccharides and 30% inulin.

The general composition of an infant formula according to the invention will now be described by way of example. The formula contains a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired.

The proteins may be intact or hydrolysed or a mixture of intact and hydrolysed proteins. It may be desirable to supply partially hydrolysed proteins (degree of hydrolysis between 2 and 20%), for example for infants believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

An infant formula according to the present invention contains a carbohydrate source. Any carbohydrate source conventionally found in infant formulae such as lactose, saccharose, maltodextrin, starch and mixtures thereof may be used although the preferred source of carbohydrates is lactose. Preferably the carbohydrate sources contribute between 35 and 65% of the total energy of the formula.

An infant formula according to the present invention contains a source of lipids. The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The infant formula will also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like.

The infant formula may optionally contain other substances which may have a beneficial effect such as lactoferrin, nucleotides, nucleosides, and the like.

Finally, the formula will contain 2FL in a total amount between 0.1 to 3 g of 2FL/100 g formula and *Bifidobacterium lactis* CNCM I-3446 in an amount of 2.10e7 cfu/g of formula.

The formula may be prepared in any suitable manner. For example, it may be to prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The 2FL may be added at this stage. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight. The 2FL may be added at this stage by dry-mixing along with the probiotic.

In another embodiment, the composition may be a supplement including the fucosylated oligosaccharide and probiotic in an amount sufficient to achieve the desired effect in an individual. This form of administration is more suited to older children and adults. Preferably the daily dose of the fucosylated oligosaccharide is from 0.1 to 3 g and the daily dose of the probiotic is from 10e5 to 10e12 cfu. The amounts of fucosylated oligosaccharide and probiotic to be included in the supplement will be selected accordingly depending upon how the supplement is to be administered. For example, if the supplement is to be administered twice a day, each supplement may contain 0.05 to 1.5 g fucosylated oligosaccharide and 10e3 to 10e6 cfu of probiotic. The supplement may be in the form of tablets, capsules, pastilles or a liquid for example. The supplement may further contain protect hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or enteral administration as well as vitamins, minerals trace elements and other micronutrients in accordance with the recommendations of Government bodies such as the USRDA.

EXAMPLE 1

An example of the composition of an infant formula according to the present invention is given below. This composition is given by way of illustration only.

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (70% FOS, 30% inulin) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| 2FL (mg) | 0.3 | 2.0 |
| *B. lactis* CNCM I-3446 | $2.10^7$ cfu/g of powder, live bacteria | |

The invention claimed is:

1. A composition suitable for use in the prevention of opportunistic infections in immune-compromised individuals, the composition comprising:
a probiotic selected from the group consisting of *Bifidobacterium lactis* CNCM I-3446 and *Bifidobacterium longum* ATCC BAA-999; and
a fucosylated oligosaccharide consisting of 2'-fucosyllactose, wherein the composition is selected from the group consisting of an infant formula and a supplement, and wherein the 2'-fucosyllactose is obtained by a process comprising a step selected from the group consisting of isolation from a natural source, chemical synthesis and biotechnological synthesis, and the 2'-fucosyllactose is present in an amount of 0.1 to 3 g per 100 g of the composition.

2. The composition of claim 1, which is an infant formula.

3. The composition of claim 2, which comprises from 10e3 to 10e12 cfu of the probiotic/g infant formula.

4. The composition of claim 2, which comprises from 10e6 to 10e9 cfu of the probiotic/g infant formula.

5. The composition of claim 2, which comprises at least one prebiotic in an amount of from 0.3 to 10% by weight of the composition.

6. The composition of claim 1, which is a supplement and which comprises from 10e5 to 10e12 cfu of the probiotic per unit dose.

7. A composition suitable for use in the prevention of opportunistic infections in immune-compromised individuals, the composition comprising:
a probiotic selected from the group consisting of *Bifidobacterium lactis* CNCM I-3446 and *Bifidobacterium longum* ATCC BAA-999; and
a fucosylated oligosaccharide consisting of 2'-fucosyllactose, wherein the composition is selected from the group consisting of an infant formula and a supplement, and wherein the 2'-fucosyllactose is obtained by a process comprising a step selected from the group consisting of isolation from a natural source, chemical synthesis and biotechnological synthesis.

* * * * *